(12) United States Patent
Faulhaber

(10) Patent No.: US 11,633,219 B2
(45) Date of Patent: Apr. 25, 2023

(54) FENESTRATED PEDICLE NAIL

(71) Applicant: GLOBUS MEDICAL, INC., Audubon, PA (US)

(72) Inventor: Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 383 days.

(21) Appl. No.: 16/452,645

(22) Filed: Jun. 26, 2019

(65) Prior Publication Data

US 2020/0405362 A1   Dec. 31, 2020

(51) Int. Cl.
*A61B 17/84* (2006.01)
*A61B 17/70* (2006.01)

(52) U.S. Cl.
CPC ........ *A61B 17/846* (2013.01); *A61B 17/7032* (2013.01); *A61B 17/7035* (2013.01)

(58) Field of Classification Search
CPC .................... A61B 17/70–7098; A61B 17/846
See application file for complete search history.

(56) References Cited

U.S. PATENT DOCUMENTS

| | | |
|---|---|---|
| 4,103,683 A | 8/1978 | Neufeld |
| 4,135,507 A | 1/1979 | Harris |
| 4,169,470 A | 10/1979 | Ender et al. |
| 4,441,492 A | 4/1984 | Rydell et al. |
| 4,541,424 A | 9/1985 | Grosse et al. |
| 4,667,664 A | 5/1987 | Taylor et al. |
| 4,878,915 A | 11/1989 | Brantigan |
| 4,952,213 A | 8/1990 | Bowman et al. |
| 4,978,349 A | 12/1990 | Frigg |
| 5,041,115 A | 8/1991 | Frigg et al. |
| 5,167,666 A | 12/1992 | Mattheck et al. |
| 5,234,434 A | 8/1993 | Goble et al. |
| 5,267,958 A | 12/1993 | Buchbinder et al. |
| 5,433,720 A | 7/1995 | Facciolo et al. |
| 5,499,986 A | 3/1996 | Dimarco |
| 5,549,610 A | 8/1996 | Russell et al. |
| 5,613,971 A | 3/1997 | Lower et al. |
| 5,674,225 A | 10/1997 | Muller |
| 5,728,128 A | 3/1998 | Crickenberger et al. |
| 5,741,256 A | 4/1998 | Bresina |
| 5,743,908 A | 4/1998 | Kim |
| 5,899,906 A | 5/1999 | Schenk |
| 6,010,506 A | 1/2000 | Gosney et al. |

(Continued)

FOREIGN PATENT DOCUMENTS

| | | |
|---|---|---|
| CA | 2373716 A1 | 11/2001 |
| CN | 201578353 U | 9/2010 |

(Continued)

*Primary Examiner* — Nicholas J Plionis

(57) ABSTRACT

Embodiments are directed to spinal treatments and, more particularly, to a fenestrated pedicle nail, wherein the pedicle nail performs as an anchored system for pedicle instrument constructs that prevents fracturing from over-compressing of bone of poor quality. Embodiments include a pedicle nail comprising a shank and a nail head. The shank may comprise a proximal end and a distal bone engagement end. The nail head may be disposable on the proximal end of the shank, wherein the nail head may threadably engage the proximal end thereof. The nail head may have external bone threads.

12 Claims, 14 Drawing Sheets

(56) References Cited

U.S. PATENT DOCUMENTS

| | | |
|---|---|---|
| 6,016,727 A | 1/2000 | Morgan |
| 6,106,528 A | 8/2000 | Durham et al. |
| 6,120,504 A | 9/2000 | Brumback et al. |
| 6,210,414 B1 | 4/2001 | Lin |
| 6,235,031 B1 | 5/2001 | Hodgeman et al. |
| 6,319,253 B1 | 11/2001 | Ackeret et al. |
| 6,187,007 B1 | 12/2001 | Frigg et al. |
| 6,406,477 B1 | 6/2002 | Fujiwara |
| 6,409,730 B1 | 6/2002 | Green et al. |
| 6,436,100 B1 | 8/2002 | Berger |
| 6,461,360 B1 | 10/2002 | Adam |
| 6,547,791 B1 | 4/2003 | Buhren et al. |
| 6,565,573 B1 | 5/2003 | Ferrante et al. |
| 6,702,816 B2 | 3/2004 | Buhler |
| 6,835,197 B2 | 12/2004 | Roth et al. |
| 6,908,465 B2 | 6/2005 | von Hoffmann et al. |
| 6,926,707 B2 | 8/2005 | Nash et al. |
| 7,217,246 B1 | 5/2007 | Stone |
| 7,247,156 B2 | 7/2007 | Ekholm et al. |
| 7,311,710 B2 | 12/2007 | Zander |
| 7,410,488 B2 | 8/2008 | Janna et al. |
| 7,476,225 B2 | 1/2009 | Cole |
| 7,549,994 B2 | 6/2009 | Zander et al. |
| 7,621,913 B2 | 11/2009 | Semet |
| 7,686,808 B2 | 3/2010 | Orbay et al. |
| 7,722,611 B2 | 5/2010 | Cavallazzi et al. |
| 7,763,022 B2 | 7/2010 | Speitling et al. |
| 7,780,667 B2 | 8/2010 | Wantanabe et al. |
| 7,799,030 B2 | 9/2010 | Wantanabe et al. |
| 7,837,709 B2 | 11/2010 | Dutoit et al. |
| 7,914,532 B2 | 3/2011 | Shaver et al. |
| 7,927,336 B2 | 4/2011 | Rasmussen |
| D638,125 S | 5/2011 | Velikov |
| D638,126 S | 5/2011 | Velikov |
| 8,057,476 B2 | 11/2011 | Ekholm et al. |
| 8,083,742 B2 | 12/2011 | Martin |
| 8,092,454 B2 | 1/2012 | Sohngen |
| 8,100,911 B2 | 1/2012 | Yamazaki et al. |
| 8,114,079 B2 | 2/2012 | Haidukewych et al. |
| 8,137,348 B2 | 3/2012 | Gotfried |
| 8,172,841 B2 | 5/2012 | Defossez |
| 8,187,281 B2 | 5/2012 | Cresina et al. |
| 8,187,309 B2 | 5/2012 | Castaneda et al. |
| 8,241,286 B2 | 8/2012 | Metzinger et al. |
| 8,262,658 B2 | 9/2012 | Schlienger et al. |
| 8,277,450 B2 | 10/2012 | Dees, Jr. et al. |
| 8,303,590 B2 | 11/2012 | Elghazaly et al. |
| 8,317,788 B2 | 11/2012 | Kaup |
| 8,317,789 B2 | 11/2012 | LeCronier et al. |
| 8,328,805 B2 | 12/2012 | Cole |
| 8,360,970 B2 | 1/2013 | Mangiardi |
| 8,414,584 B2 | 4/2013 | Brigido |
| 8,449,544 B2 | 5/2013 | Grusin |
| 8,454,606 B2 | 6/2013 | Frigg et al. |
| 8,491,584 B1 | 7/2013 | Fagan |
| 8,518,040 B2 | 8/2013 | Schlienger et al. |
| RE44,501 E | 9/2013 | Janna et al. |
| 8,562,606 B2 | 10/2013 | Richter et al. |
| 8,585,744 B2 | 11/2013 | Duggal et al. |
| 8,591,513 B2 | 11/2013 | Overes et al. |
| 8,668,695 B2 | 3/2014 | Schwammberger et al. |
| 8,715,283 B2 | 5/2014 | Brumfield et al. |
| 8,740,902 B2 | 6/2014 | Brodsky et al. |
| 8,764,752 B2 | 7/2014 | Buettler et al. |
| 8,790,343 B2 | 7/2014 | McClellan et al. |
| 8,808,292 B2 | 8/2014 | Velikov |
| 8,808,293 B2 | 8/2014 | Buettler et al. |
| 8,834,469 B2 | 9/2014 | Wantanabe et al. |
| 8,906,023 B2 | 12/2014 | Matityahu et al. |
| 8,932,301 B2 | 1/2015 | Metzinger et al. |
| 8,945,136 B2 | 2/2015 | Overes et al. |
| 8,961,518 B2 | 2/2015 | Taylor et al. |
| 8,992,587 B2 | 3/2015 | Kirschman |
| 9,072,552 B2 | 7/2015 | Simon et al. |
| 9,101,432 B2 | 8/2015 | Limouze et al. |
| 9,119,645 B2 | 9/2015 | McBride |
| 9,138,278 B2 | 9/2015 | Van Osten, III |
| 9,155,582 B2 | 10/2015 | Felder et al. |
| 9,173,692 B1* | 11/2015 | Kaloostian ......... A61B 17/8615 |
| 9,295,504 B2 | 3/2016 | Haidukewych et al. |
| 9,358,049 B2 | 6/2016 | Simon et al. |
| RE46,078 E | 7/2016 | Janna et al. |
| 9,387,019 B2 | 7/2016 | Duggal et al. |
| 9,393,064 B2 | 7/2016 | Roethlisberger et al. |
| 9,408,645 B2 | 8/2016 | Graca et al. |
| 9,421,049 B2 | 8/2016 | Rogachefsky |
| 9,427,266 B2 | 8/2016 | Kmiec, Jr. |
| 9,433,448 B2 | 9/2016 | Ehmke et al. |
| 9,474,557 B2 | 10/2016 | Schwammberger et al. |
| 9,241,744 B2 | 11/2016 | Blake et al. |
| 9,532,818 B2 | 1/2017 | Schwammberger et al. |
| 9,597,129 B2 | 3/2017 | Keller et al. |
| 9,675,363 B2 | 6/2017 | Abbasi |
| 9,724,108 B2 | 8/2017 | Prien |
| 10,653,455 B2* | 5/2020 | Lehman, Jr. ......... A61B 17/7037 |
| 2003/0018340 A1 | 1/2003 | Branch |
| 2006/0111716 A1 | 5/2006 | Schlienger et al. |
| 2006/0200160 A1 | 9/2006 | Border et al. |
| 2007/0118119 A1 | 5/2007 | Hestad |
| 2008/0154264 A1 | 6/2008 | Wack et al. |
| 2008/0294260 A1* | 11/2008 | Gray ............... A61B 17/8047 |
| | | 623/17.16 |
| 2009/0088604 A1 | 4/2009 | Lowry et al. |
| 2010/0016903 A1* | 1/2010 | Matityahu ........... A61B 17/866 |
| | | 606/301 |
| 2010/0234846 A1 | 9/2010 | Eglseder |
| 2010/0274254 A1 | 10/2010 | Boileau et al. |
| 2011/0196372 A1 | 8/2011 | Murase |
| 2011/0245885 A1 | 10/2011 | Powell |
| 2012/0215264 A1* | 8/2012 | Lee ................ A61B 17/8685 |
| | | 606/305 |
| 2013/0190570 A1 | 6/2013 | Hirsch et al. |
| 2013/0282016 A1 | 10/2013 | Volpi et al. |
| 2013/0289572 A1 | 10/2013 | Broome |
| 2013/0317502 A1 | 11/2013 | Overes et al. |
| 2013/0325076 A1 | 12/2013 | Palmer et al. |
| 2014/0142632 A1* | 5/2014 | Keyer ............... A61B 17/7077 |
| | | 606/265 |
| 2014/0243838 A1 | 8/2014 | Feibel et al. |
| 2014/0276828 A1 | 9/2014 | Howling et al. |
| 2014/0277162 A1* | 9/2014 | Kostuik ............. A61B 17/1642 |
| | | 606/278 |
| 2014/0309648 A1 | 10/2014 | Matityahu |
| 2015/0038967 A1 | 2/2015 | Khong et al. |
| 2015/0080972 A1* | 3/2015 | Chin ................. A61B 17/863 |
| | | 606/304 |
| 2015/0150567 A1 | 6/2015 | Okuno et al. |
| 2015/0265323 A1 | 9/2015 | Sems et al. |
| 2015/0282843 A1* | 10/2015 | Spitler ............. A61B 17/7082 |
| | | 606/266 |
| 2016/0030064 A1 | 2/2016 | Dacosta et al. |
| 2016/0051295 A1 | 2/2016 | Nakamura et al. |
| 2016/0089189 A1 | 3/2016 | Buscaglia et al. |
| 2016/0256202 A1 | 9/2016 | Halder |
| 2016/0262819 A1 | 9/2016 | May et al. |
| 2016/0278815 A1* | 9/2016 | Fitzpatrick ......... A61F 2/30942 |
| 2017/0112555 A1 | 4/2017 | Wallenstein ....... A61B 17/8615 |
| 2017/0202566 A1 | 7/2017 | Luo et al. |
| 2018/0338761 A1* | 11/2018 | Moskowitz ........ A61B 17/7001 |
| 2020/0022817 A1* | 1/2020 | Crossgrove ......... A61B 17/863 |
| 2020/0054363 A1* | 2/2020 | Dechelette ......... A61B 17/7032 |
| 2021/0212733 A1* | 7/2021 | Mehl ................ A61B 17/864 |

FOREIGN PATENT DOCUMENTS

| | | |
|---|---|---|
| DE | 3722852 A1 | 1/1989 |
| DE | 4240277 A1 | 6/1993 |
| DE | 102008020193 A1 | 10/2009 |
| DE | 102014109935 A1 | 10/2009 |
| DE | 102009010328 A1 | 8/2010 |
| EP | 257118 | 3/1988 |
| EP | 2548523 A1 | 1/2013 |
| FR | 2965471 | 4/2012 |

(56) References Cited

FOREIGN PATENT DOCUMENTS

| | | |
|---|---|---|
| JP | 2973316 B1 | 11/1999 |
| JP | 2000342596 | 12/2000 |
| WO | 2016059347 A1 | 4/2016 |
| WO | 2016082861 A1 | 6/2016 |

* cited by examiner

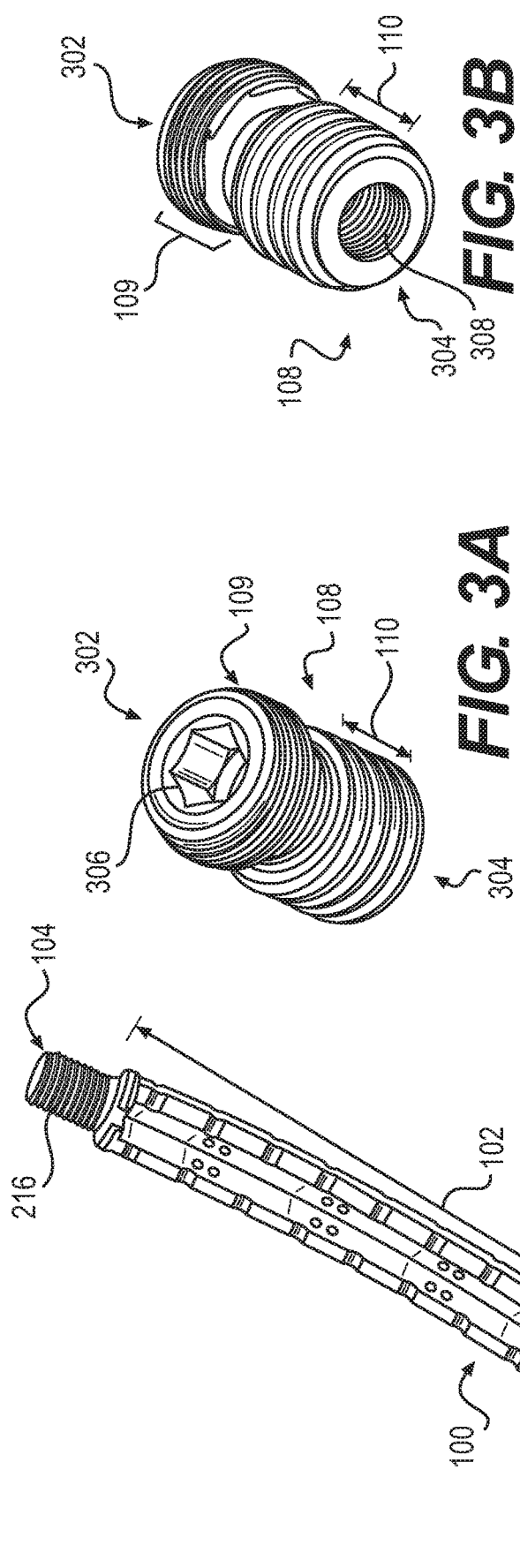
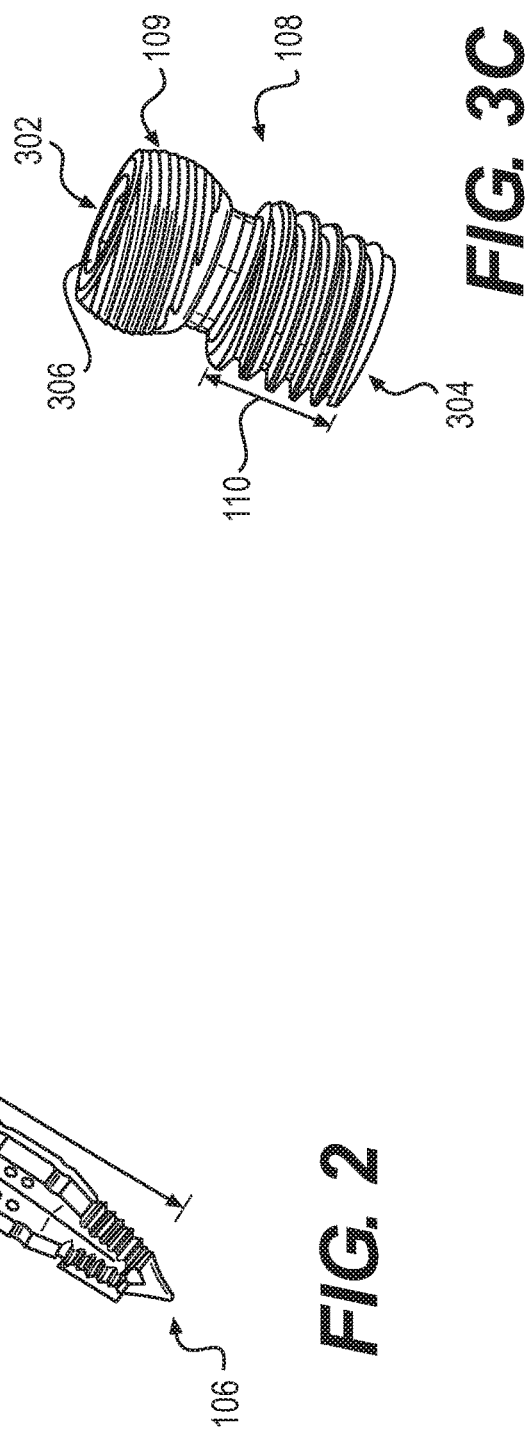

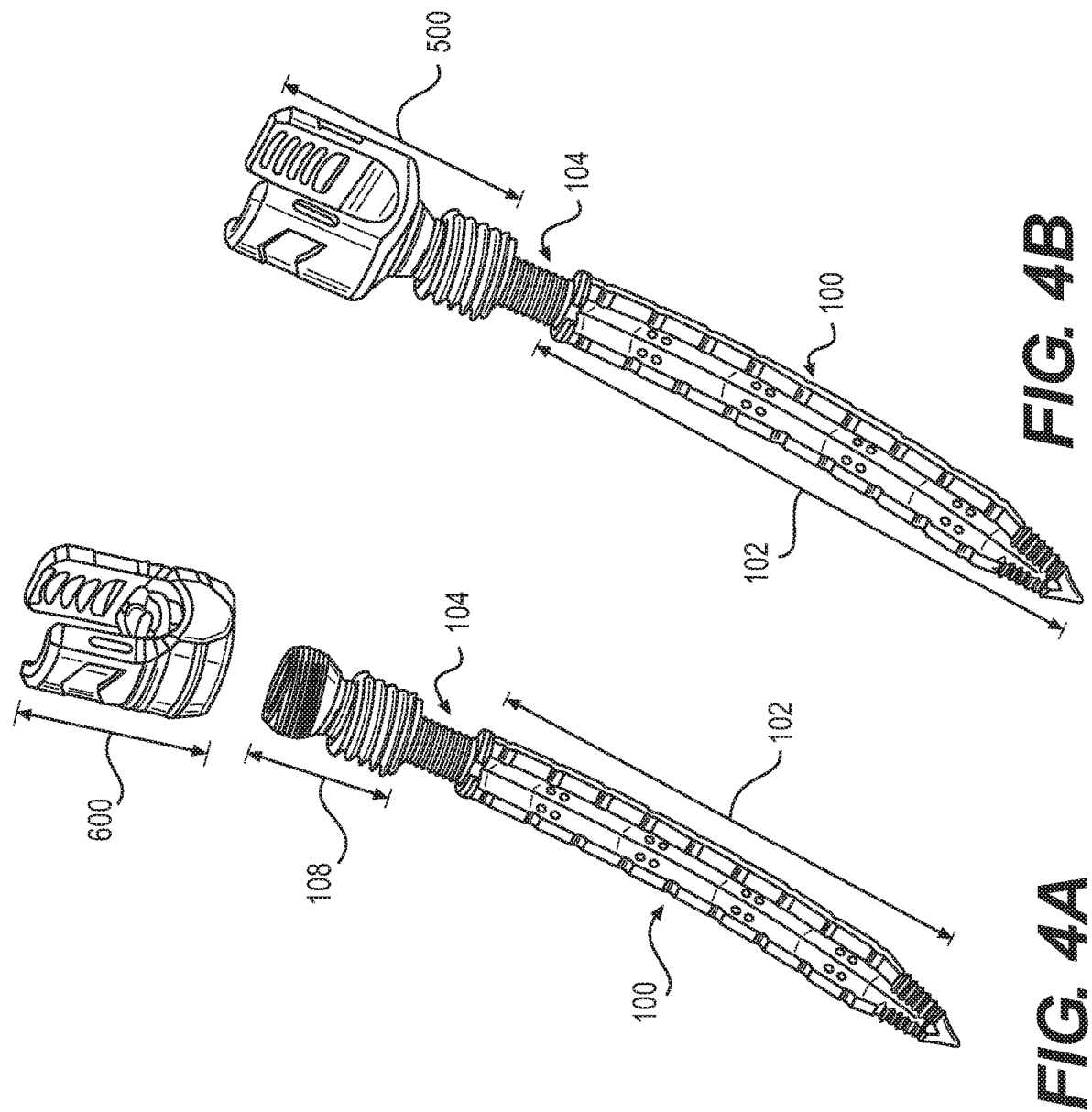

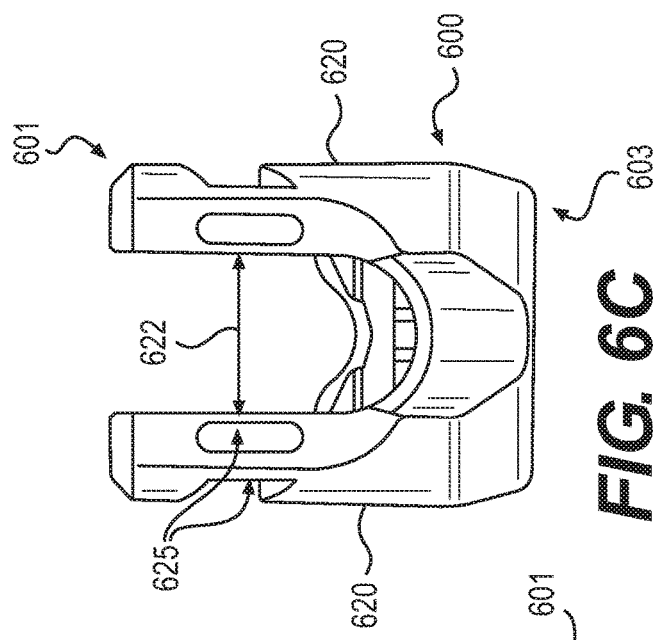
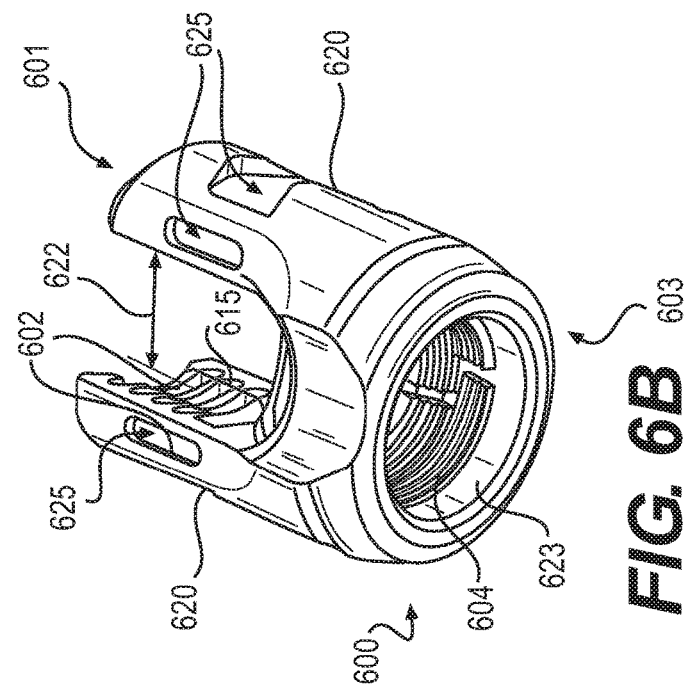
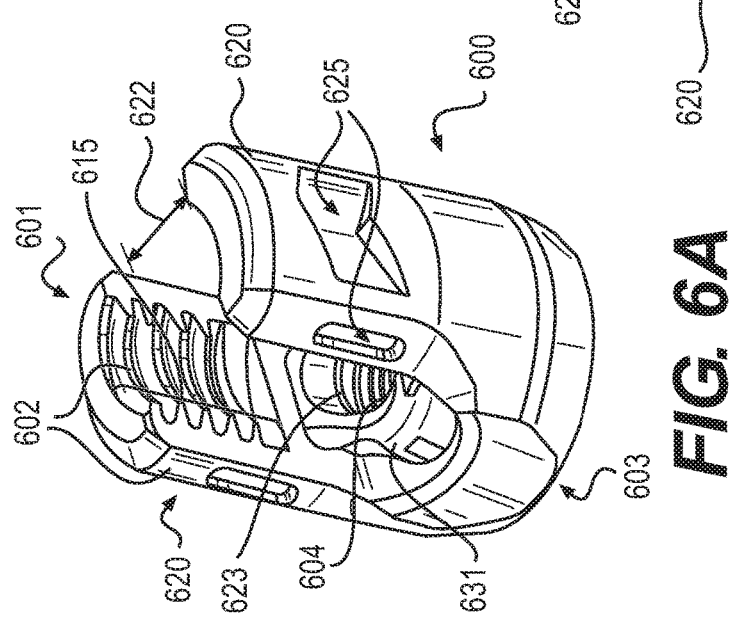

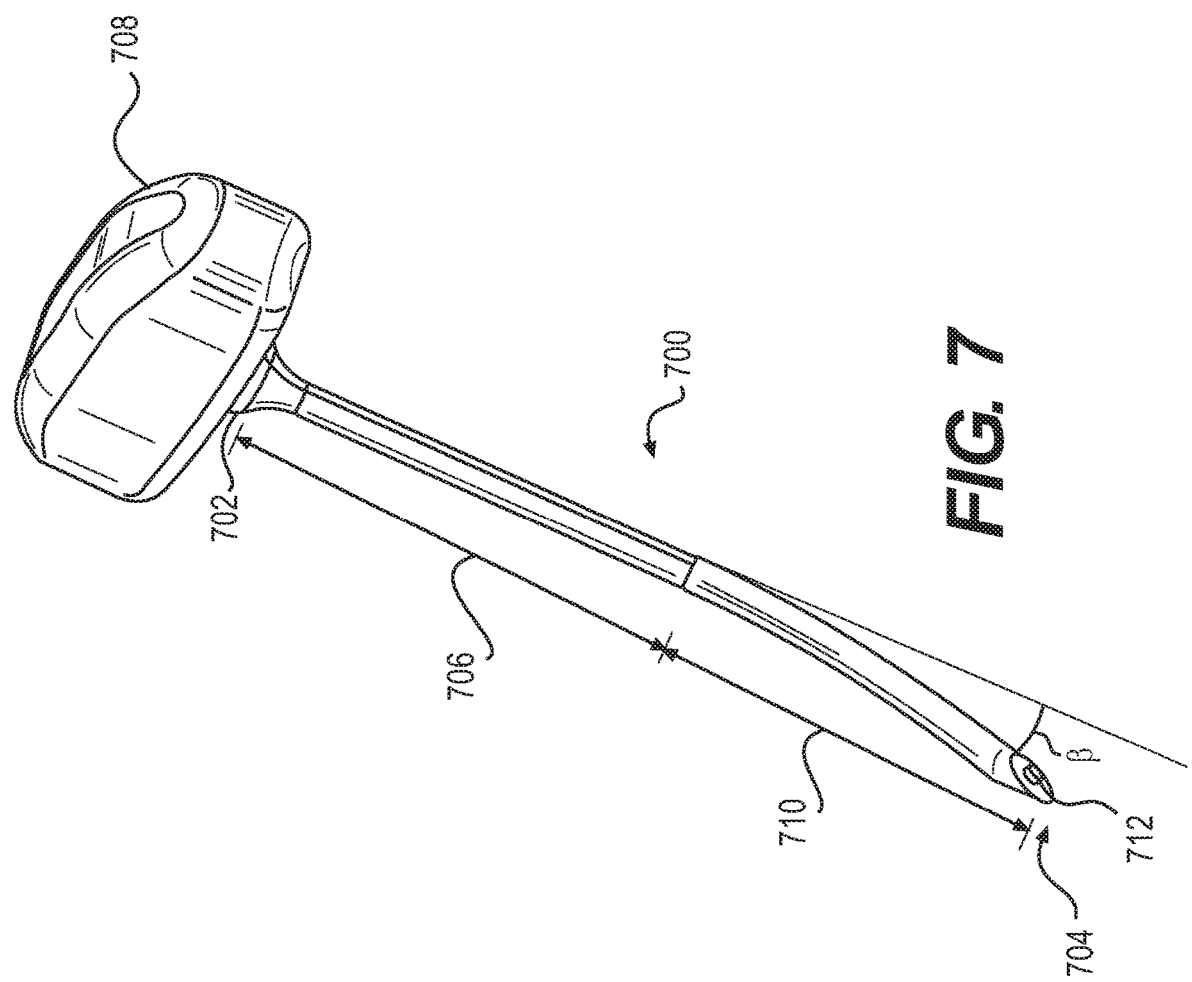

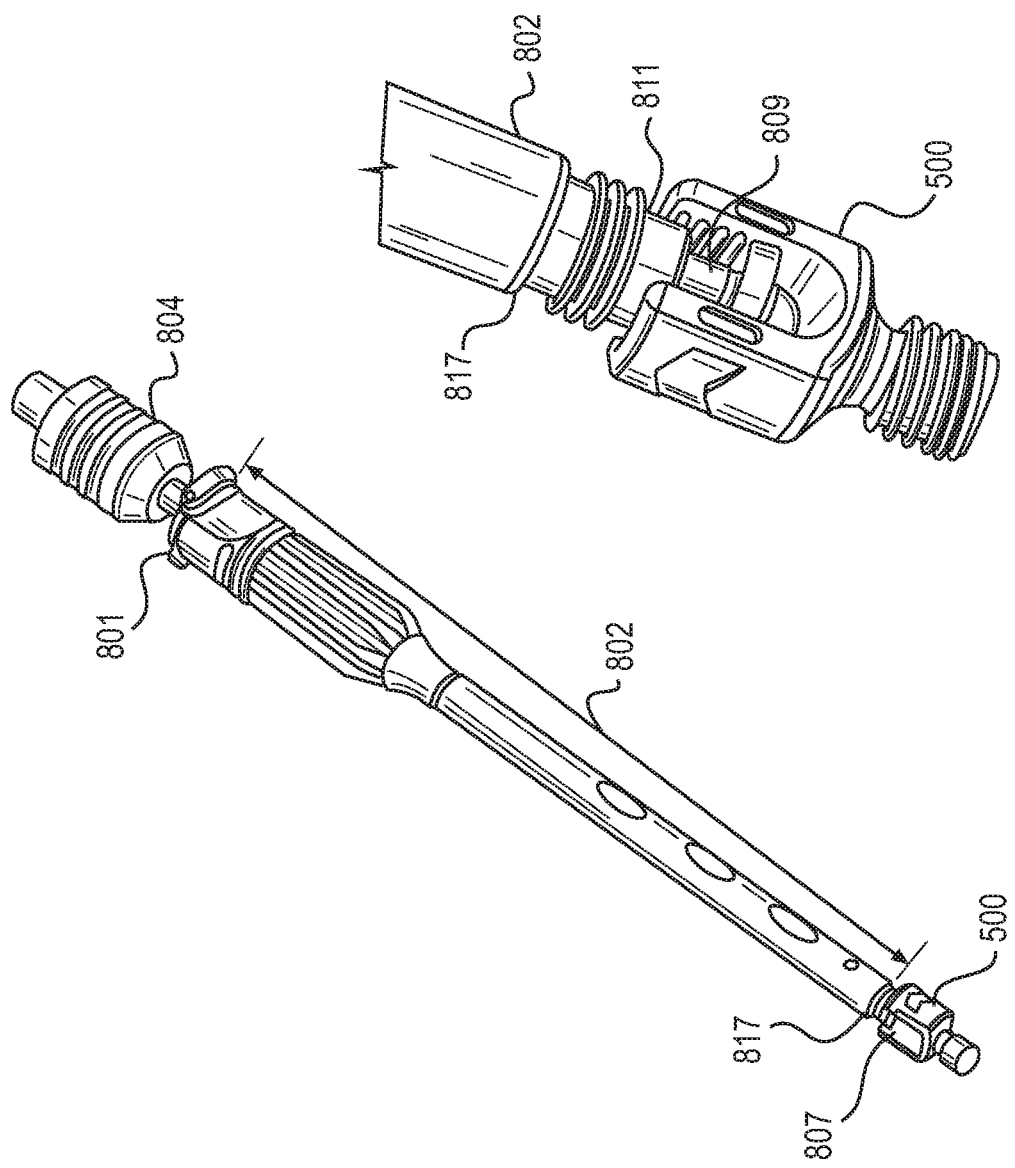

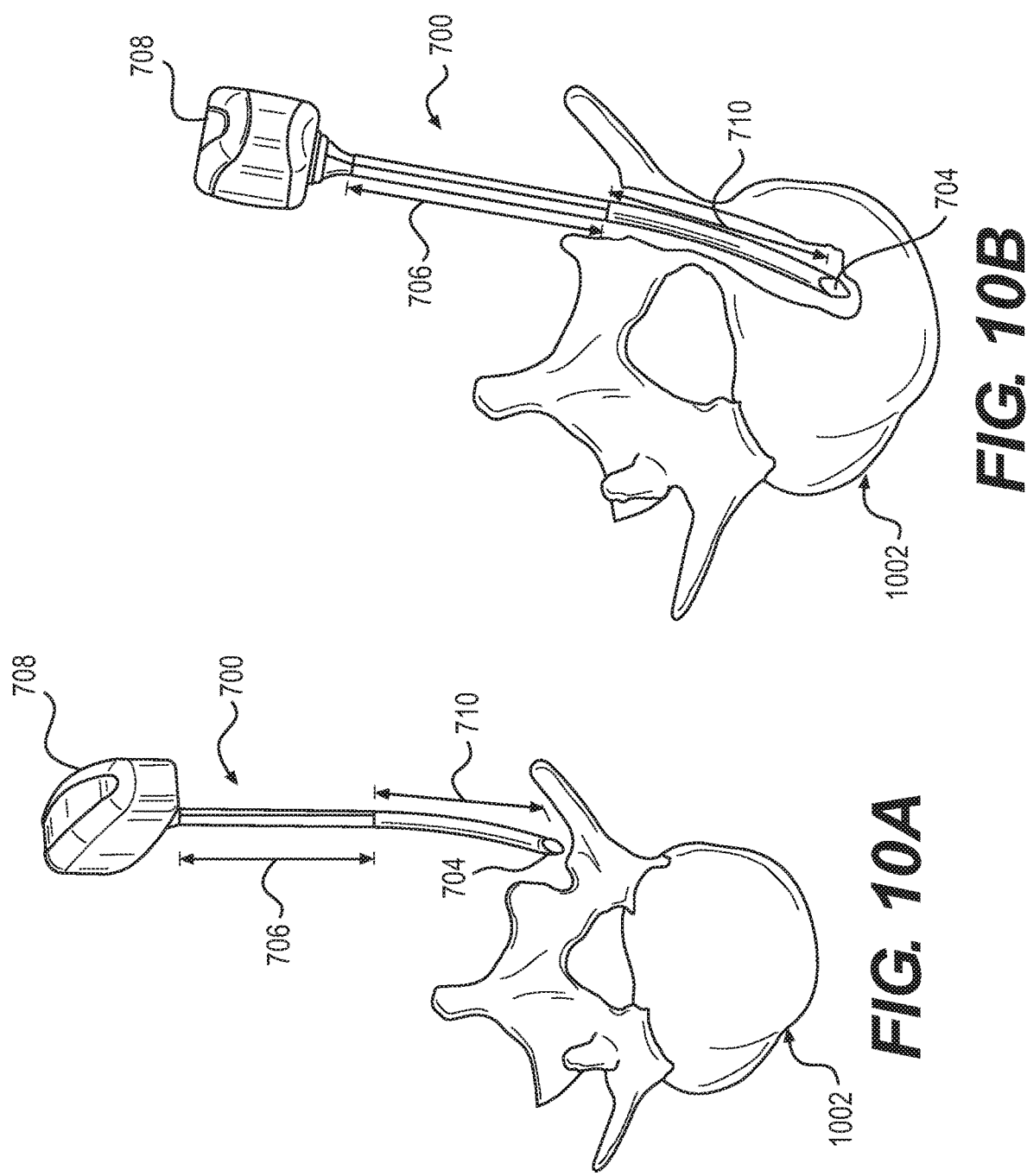

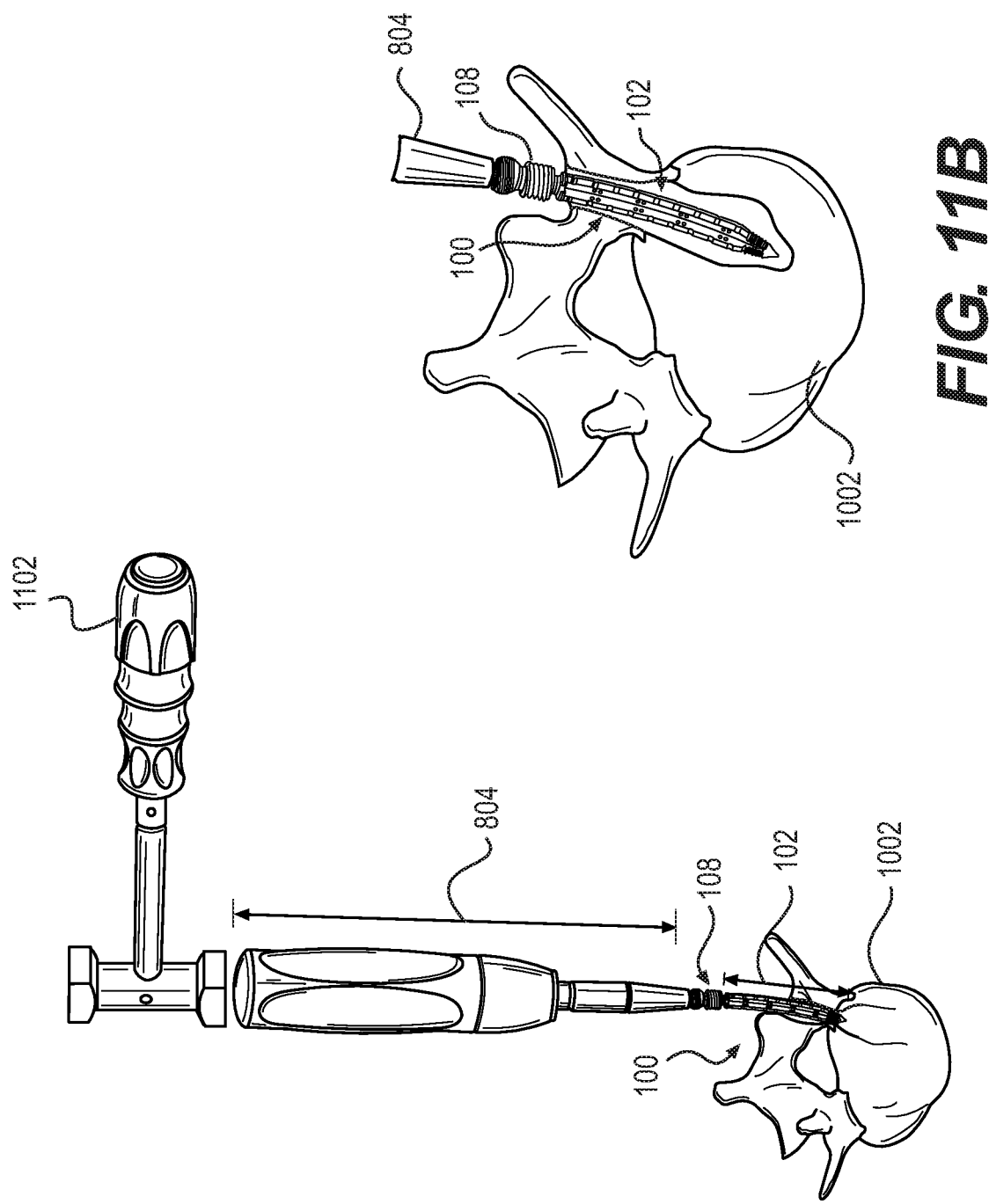

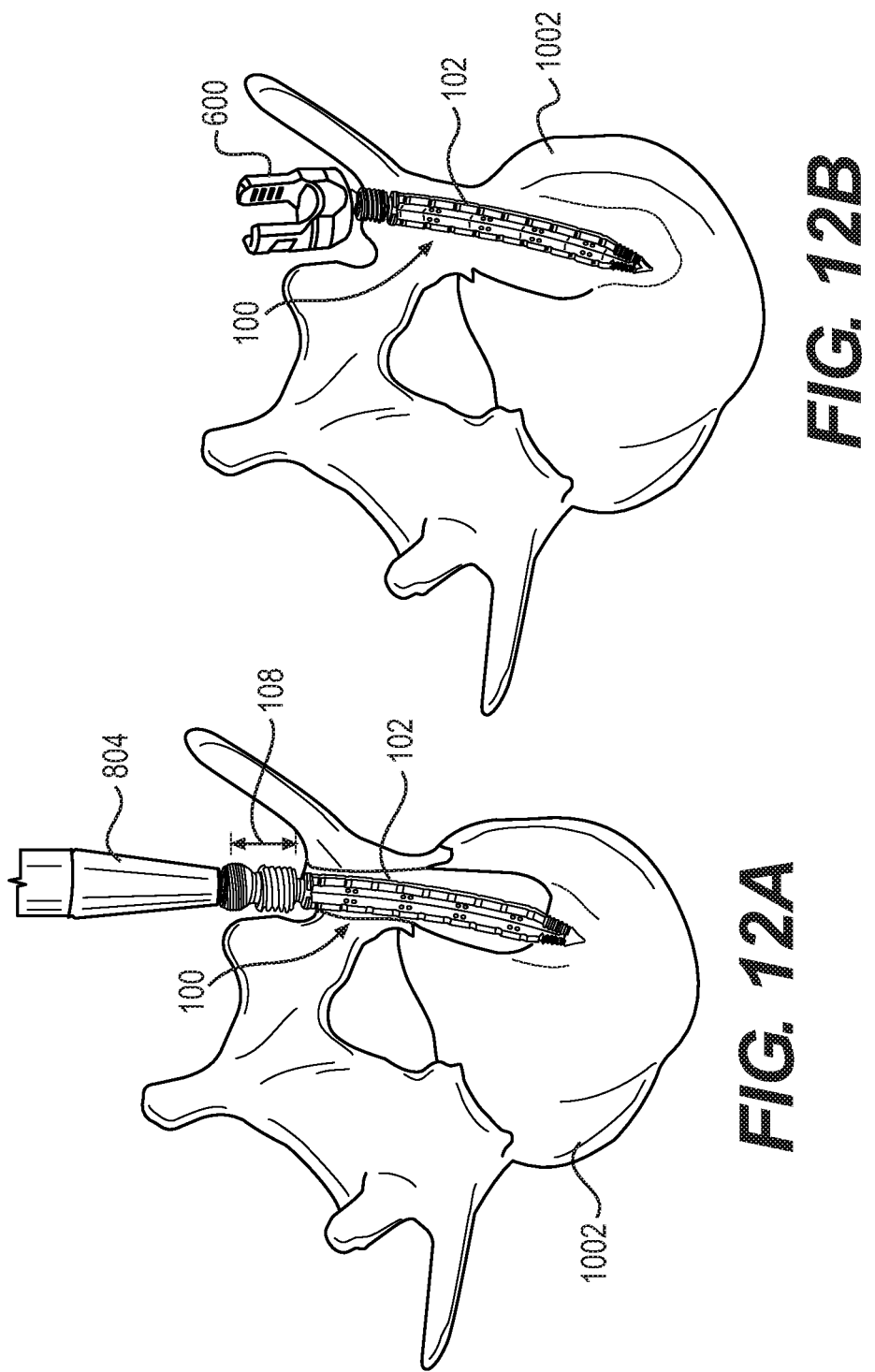

FENESTRATED PEDICLE NAIL

BACKGROUND

Many types of spinal irregularities can cause pain, limit range of motion, or injure the nervous system within the spinal column. These irregularities can result from, without limitation, trauma, tumor, disc degeneration, and disease. Often, these irregularities may be treated by immobilizing a portion of the spine. This treatment typically may involve affixing a plurality of screws and/or hooks to one or more vertebrae and connecting the screws or hooks to an elongated rod that generally extends in the direction of the spine.

Treatment for these spinal irregularities often involves using a system of pedicle screws and rods to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. In many cases, an anchoring member such as a pedicle screw along with a vertical solid member may help restore spinal elements to a pain free situation, or at least may help reduce pain or prevent further injury to the spine.

A pedicle screw system is sometimes used as an adjunct to spinal fusion surgery, thereby providing a means of gripping a spinal segment. A conventional pedicle screw system may comprise a pedicle screw and a receiving device. The pedicle screw may include an externally threaded stem and a head portion. The rod-receiving device may couple to the head portion of the pedicle screw and can receive a rod, commonly referred to as a distraction rod. Two such systems may be inserted into respective vertebrae and adjusted to distract and/or stabilize a spinal column, for instance during an operation to correct a herniated disk. The pedicle screw does not, by itself, fixate the spinal segment, but instead may operate as an anchor point to receive the rod-receiving device, which in turn receives the rod. One goal of such a system may be to substantially reduce and/or prevent relative motion between the spinal segments that are being fused.

Although the pedicle screw minimizes relative motion between the spinal segments, the pedicle screw is still subject to windshield-wiper loosening, which can potentially result in pull out of the pedicle screw. Accordingly, there exists a need to further decrease axial motion.

SUMMARY

A first exemplary embodiment provides a pedicle nail that may comprise a shank and a nail head. The shank may comprise a proximal end and a distal bone engagement end. The nail head may be disposable on the proximal end of the shank, wherein the nail head may threadably engage the proximal end, and wherein the nail head can have external bone threads.

A second exemplary embodiment provides a pedicle nail system that may comprise a pedicle nail and a tulip. The pedicle nail may comprise a shank, wherein the shank may comprise a proximal end and a distal bone engagement end, wherein the proximal end may comprise mounting threads attached thereto. The tulip may comprise a proximal end and a distal end A third exemplary embodiment provides a pedicle nail system that may comprise a pedicle nail, a tulip, and a driver. The pedicle nail may comprise a shank, wherein the shank may comprise a proximal end and a distal bone engagement end, wherein the proximal end may comprise mounting threads attached thereto. The tulip may comprise a proximal end and a distal end, wherein the tulip may be configured to be mounted on the pedicle nail. The driver may comprise a proximal end and a distal end; wherein the distal end of the driver is removably connected to the proximal end of the insertion tool assembly.

Further areas of applicability of the present invention will become apparent from the detailed description provided hereinafter. It should be understood that the detailed description and the specific examples, while indicating the preferred or exemplary embodiments of the invention, are intended for purposes of illustration only and are not intended to limit the scope of the invention.

BRIEF DESCRIPTION OF THE DRAWINGS

These drawings illustrate certain aspects of some examples of the present disclosure, and should not be used to limit or define the disclosure, wherein:

FIG. 2 illustrates an embodiment of a fenestrated pedicle nail without the nail head connected thereto;

FIGS. 3A, 3B, and 3C illustrate an embodiment of a nail head;

FIGS. 4A and 4B illustrate embodiments of a fenestrated pedicle nail with a tulip connected thereto;

FIGS. 6A, 6B, and 6C illustrate an embodiment of a polyaxial tulip;

FIG. 7 illustrates an embodiment of a curved awl; and

FIGS. 8A, 8B, 8C and 8D illustrate an embodiment of a monoaxial insertion tool assembly comprising a threaded shaft locking assembly for a monoaxial tulip.

FIGS. 10A and 10B illustrate an embodiment of a curved awl creating a pathway for insertion of a pedicle nail.

FIGS. 11A and 11B illustrate an embodiment of a pedicle nail system, including a driver, with a tamping device driving the pedicle nail into a cortical bone.

FIGS. 12A and 12B illustrate a polyaxial tulip insertion procedure with an embodiment of the nail head of a pedicle nail system being threaded into the cortical bone with an insertion tool assembly.

DETAILED DESCRIPTION

Embodiments are directed to spinal treatments and, more particularly, to a pedicle nail, wherein the pedicle nail performs as an anchored system for pedicle instrument constructs that prevents fracturing from over-compressing of bone of poor quality. Embodiments of the pedicle nail may be used in a wide variety of spinal treatments for treatment of spinal irregularities, where the pedicle nail can increase stability of the bone/nail interface in the cancellous region of the vertebral body; reduce pull-out of the nail from the windshield-wiper effect; minimize the diameter of the nail or other pedicle instrument needed in a revision procedure; and reduce the risk of fracturing from over-compression.

Embodiments of the pedicle nail can be implanted inside a cancellous region of the vertebral body, attached to a nail head implanted into the cortical bone. The pedicle nail can be curved with a curvature angle θ. Hence, although a bone screw may be subject to windshield-wiper loosening, the geometry of the curved pedicle nail can change the insertion vector, thereby reducing the axial motion. In some embodiments, the difference between the pitch of the mounting thread of the pedicle nail and the bone screw thread of the nail head can decrease the chance of over-compression because the nail can be pulled toward the nail head, traveling through a cavity that was previously created using a curved awl.

In some embodiments, a medical professional (e.g., a surgeon) may first prepare for the area to be treated by creating an incision in a patient's back and adjusting the lower back muscles to access the desired area. Some embodiments may use the curved awl to create a pathway for insertion of the pedicle nail. Embodiments may then include tamping down the pedicle nail, for example, with a tamping or hammering tool, until the nail head contacts the cortical bone. In at least one embodiment, the nail head, having external bone threads thereupon, may be threaded into the cortical bone, then a polyaxial tulip may be assembled by threadable connection to the proximal end of the nail head. Alternatively, the nail head may be removed after tamping for threadable attachment of a monoaxial tulip to the proximal end of the pedicle nail. More specifically, for example, a threaded shaft locking assembly, having an outer shaft and an inner shaft, may be retracted to allow the outer shaft to be threaded into a monoaxial tulip and seated therein. The monoaxial tulip can then be threaded into the cortical bone.

Figure 1B:
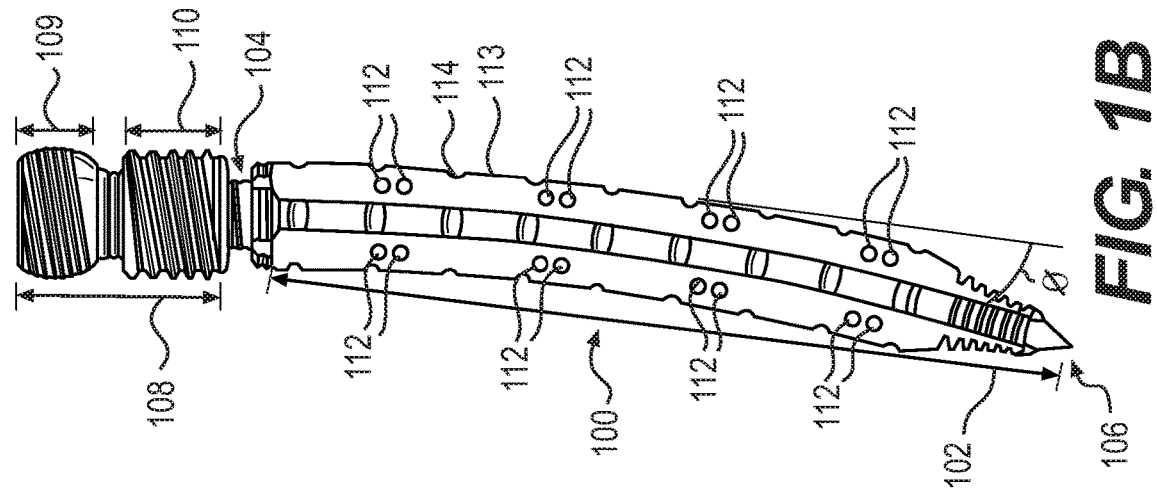
FIGS. 1A and 1B illustrate an embodiment of a fenestrated pedicle nail with the nail head connected thereto.
Figure 1A:
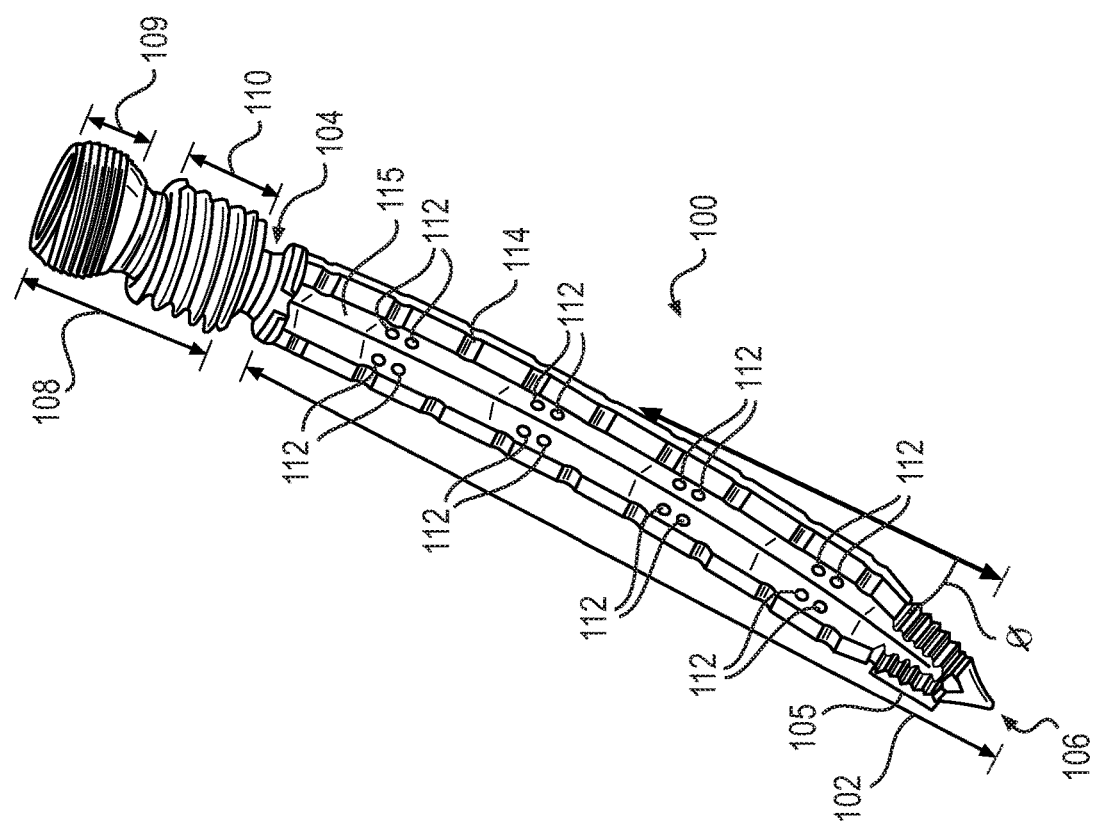

FIGS. 1A, and 1B illustrate a pedicle nail 100 in accordance with example embodiments. In the illustrated embodiment, the pedicle nail 100 comprises a shank 102 having a proximal end 104 and a distal bone engagement end 106. As illustrated, the distal bone engagement end 106 may include bone threads or notches 105 thereabout. Embodiments of the pedicle nail 100 may further include a nail head 108 disposable on the proximal end 104 of the shank 102. As illustrated, the nail head 108 may threadingly engage the proximal end 104 of the shank 102. Embodiments of the nail head 108 may also include external bone threads 110. The nail head 108 will be described in more detail below with respect to FIGS. 3A, 3B, and 3C.

In the illustrated embodiment, the pedicle nail 100 has fenestrated perforations 112 positioned about the longitudinal axis of the shank 102. Accordingly, embodiments of the pedicle nail 100 may be referred as "fenestrated." However, it should be understood that the fenestrated perforations 112 are optional and embodiments of the pedicle nail 100 may not include the fenestrated perforations 112. The shank 102 may also include at least two protrusions configured along the longitudinal axis, wherein the protrusions 113 form channels 115 along the longitudinal axis of the shaft 102. The protrusions 113 may have an exposed vertical edge, wherein the vertical edge may have at least two notches 114 therein, wherein the notches 114 may be in vertical alignment with one another.

As illustrated, the shank 102 can be a curved shank, having a curvature angle θ. The shank 102 can have any suitable curvature angle θ. Those with ordinary skill in the art will appreciate the curved shank 102, in that the curvature angle θ may allow for rotational movement or angular adjustment of the pedicle nail 100 in connection with bone structures. Moreover, the curved shank 102 may have several additional features, including, but not limited to, thread pitch, shank diameter to thread diameter, overall shank shape, and the like, depending, for example, on the particular application.

Specifically referring to FIG. 2, an embodiment of the pedicle nail 100 is illustrated without the nail head 108 attached thereto. As shown in FIG. 2, the shank 102 includes mounting threads 216 disposed about the proximal end 104. With additional reference to FIGS. 1A and 1B, the mounting threads 216 of the shank 102 can be threadingly connected to the nail head 108. In at least one embodiment, the pedicle nail 100 can include differences in pitch between the mounting threads 216 and the nail head bone threads 110 of the nail head 108. Pitch is the distance between threads and may be expressed in millimeters. For example, a pitch of 1.25 indicates a distance between threads of 1.25 millimeters. In some embodiments, the bone threads 110 may have a pitch that is greater than a pitch of the mounting threads 216. For example, the pitch of the bone threads 110 may be greater than the pitch of the mounting threads 216 by about 0.1 millimeters, 0.2 millimeters, 0.3 millimeters, or greater. The differences in pitch can pull the pedicle nail 100 toward the nail head 108 during implantation. The pedicle nail 100 can travel through a cavity previously created by a medical professional, (e.g., a surgeon) using instruments such as a curved awl 600 (e.g., shown on FIG. 6); thereby helping to prevent over-compression.

In one embodiment (not shown), the pedicle nail 100 can be cannulated, which means a channel can extend axially through the entire length of the pedicle nail 100. For example, depending upon the specific procedure, the channel can allow the pedicle nail 100 to be maneuvered over and receive a Kirschner wire, commonly referred to as a K-wire. The K-wire can typically be pre-positioned using imaging techniques, for example, fluoroscopic imaging.

FIGS. 3A, 3B, and 3C illustrate an embodiment of a nail head 108. As illustrated, the nail head 108 may have a proximal end 302 and a distal end 304. The proximal end 302 may comprise an insertion tool assembly interface 306 affixed therein. The distal end 304 may include mounting threads 308 therein, wherein the mounting threads 308 may be designed to threadably receive the mounting threads 216 affixed atop the proximal end 104 of the shank 102 (e.g., shown on FIG. 1C) of the pedicle nail 100. The embodiment of the nail head 108 also illustrates the bone threads 110 affixed to the exterior of the nail head 108. As illustrated, the bone threads 110 may extend from the distal end 304. Moreover, the bone threads 110 may be disposed on the distal end 304, the proximal end 302, or a combination thereof. During installation, the bone threads 110 can engage cortical bone 1002 (e.g., see FIGS. 10A and 10B), for example, to secure the nail head 108. Embodiments of the nail head 108 also illustrates tulip threads 309 affixed to the exterior of the nail head 108, for example, to be threadingly received by the corresponding threads (e.g., mounting threads 604 on FIG. 6B) on a tulip (e.g., polyaxial tulip 600 shown on FIGS. 6A, 6B, and 6C). As illustrated, the tulip threads 309 may extend from the proximal end 302 and may be spaced apart from the bone threads 110.

Specifically referring to FIG. 3A, the insertion tool assembly interface 306 which may act as a tool engagement surface, for example, that may be engaged by a screwdriving tool or other device. The insertion tool assembly interface 306 may permit a physician to apply torsional or axial forces to the nail head 108 to drive the pedicle nail 100 (e.g., shown on FIGS. 1A, 1B, and 2) into the bone. In the illustrated embodiment, the insertion tool assembly interface 306 of the nail head 108 may be a polygonal recess. For instance, the polygonal recess may be a hexagonal recess that receives a hexagonal tool, such as an Allen wrench, for example. Although not shown, the insertion tool assembly interface 306 may be configured to encompass tool engagement surfaces having other shapes, such as slot or cross. In an alternative embodiment (not illustrated), the insertion tool assembly interface 306 may be configured with a protruding engagement surface that may engage with a tool or device having a corresponding recess.

FIGS. 4A and 4B illustrate embodiments of a pedicle nail 100 with a tulip, such as a monoaxial tulip 500 or a polyaxial tulip, 600, affixed thereto. FIG. 4A illustrates a polyaxial tulip 600 for mounting onto the proximal end 302 of the nail head 108. For example, the polyaxial tulip 600 may be threaded onto the tulip threads 309. FIG. 4B illustrates a monoaxial tulip 500, wherein the monoaxial tulip 500 may be configured to be threadably affixed atop the proximal end 104 of the shank 102. For example, the monoaxial tulip 500 may be threaded onto the mounting threads 116 at the proximal end 104 of the shank 102.

Figure 5A:
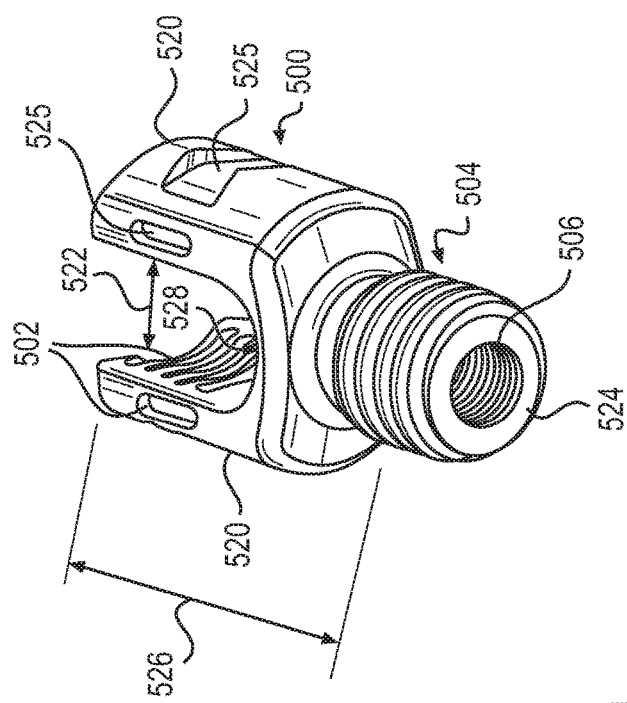
FIGS. 5A, 5B, and 5C illustrate an embodiment of a monoaxial tulip.
Figure 5B:
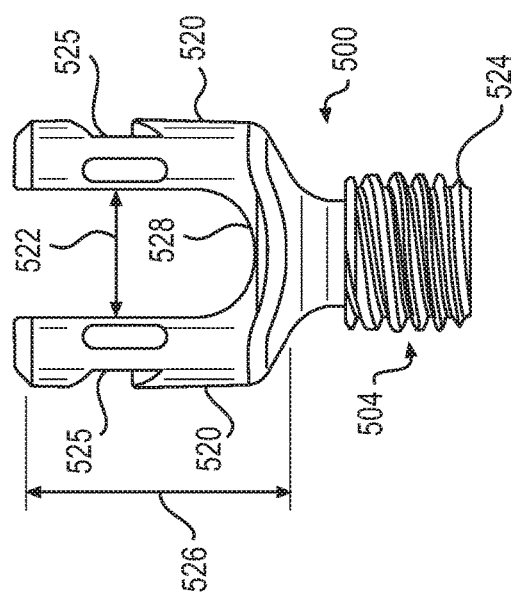
Figure 5C:
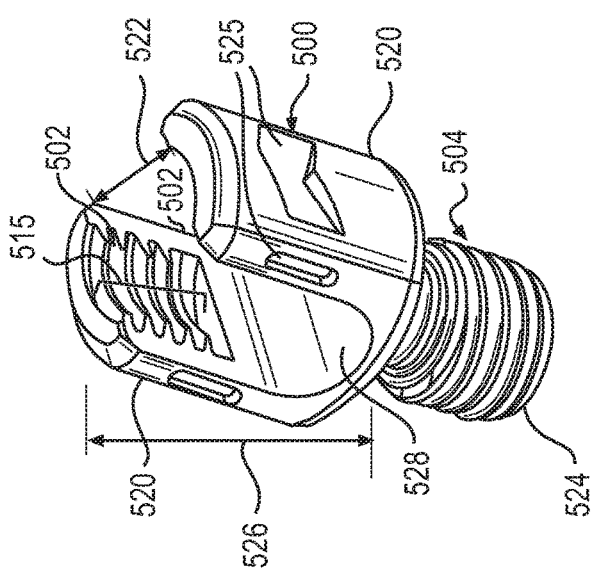

FIGS. 5A, 5B, and 5C illustrate an embodiment of a monoaxial tulip 500. A monoaxial tulip 500 may be used for connecting vertebrae to rods in spinal surgery, especially during procedures that require the pedicle nail 100 to remain immobile. For example, the monoaxial tulip 500 may be used in procedures that may require excessive tension. The tulip 500 may comprise a bottom portion or distal end 524 and sidewalls 520 that extend upwardly from the bottom portion 524. As illustrated, the sidewalls 520 may be generally parallel, and may define a recess 522 in the head 526. The sidewalls 520 may have features, such as slots, recesses, or detents 515, on an inner surface for engaging a locking assembly 807 (e.g., see FIGS. 8A, 8B, 8C, and 8D). The locking assembly 807 may comprise corresponding protrusions or slots 815 (e.g., see FIG. 8B) that permit the locking assembly 807 to engage with and rotate with respect to the head 526. The outer portion of the sidewalls 520 may comprise slots 525, or other suitable features, for receiving an instrument. The head 526 may be configured to include insertion tool assembly interface 502, wherein cortical bone threads 504 can be disposed at or near the bottom portion 524. Referring specifically to FIG. 5C, the bottom portion 524 may be configured to include mounting threads 506 disposed therein, wherein the mounting threads 506 may be configured to threadably receive and attach to the proximal end 104 of the pedicle nail 100 with threadable connection to the mounting threads 216 of the fenestrated pedicle nail 100 (e.g., shown on FIG. 2). In accordance with the embodiments, the monoaxial tulip 500 may include a seat 528, wherein the seat 528 may be U- or wedge-shaped, for example, and may be positioned in the head 526 against which an insertion tool assembly 800 may be seated and engaged. Although not shown, after the monoaxial tulip 500 has been threadably attached to the pedicle nail 100, a surgical rod may be inserted therein, wherein the surgical rod may be designed specifically for the particular pedicle nail 100 use in the procedure.

FIGS. 6A, 6B, and 6C illustrate an embodiment of a polyaxial tulip 600 that can include a proximal end 601, a distal end 603, and sidewalls 620 that extend upwardly from the distal end 603. A polyaxial tulip 600 may also be used for connecting vertebrae to rods during spinal surgery. The polyaxial tulip 600 may include a housing 631, which allows the tulip 600 a range of motion along several different axes relative to the housing 631. A ball joint (not shown) may allow a surgeon flexibility when implanting pedicle nails 100. As illustrated, the sidewalls 620 may be generally parallel, and may define a recess 622, wherein the recess 622 may surround a bore 623, where the bore 623 may have mounting threads 604 disposed therein. The bore 623 with corresponding mounting threads 604 may be configured to receive the tulip threads 109 affixed atop the proximal end 104 of the nail head 108 (e.g., shown on FIGS. 3A, 3B, and 3C). The upper portion of the sidewalls 620 may have features, such as slots, recesses, or detents 615, on an inner surface for engaging the locking assembly 807. The locking assembly 807 can comprise corresponding protrusions or slots 815 that permit the locking assembly 807 to engage with and rotate with respect to the tulip 600. The outer portion of the sidewalls 620 may comprise slots 625, or other suitable features, for receiving an instrument. The proximal end 601 may be configured to include an insertion tool assembly interface 602. The recess 622 may also provide for placement of a surgical rod (not shown), may be inserted therein, wherein the surgical rod may be designed specifically for the particular pedicle nail 100 use in the procedure.

FIG. 7 illustrates an embodiment of a curved surgical bone awl 700. As illustrated, the curved awl 700 may have a proximal end 702 with a handle 708 attached thereto, a distal end 704, and a shaft 706. In general, the surgical bone awl 700 may be provided for orthopedic applications that include creating or enlarging holes in the cortical bone 1002. As illustrated, the curved surgical bone awl 700 may have a shaft 706 and a cutting tip 710 that may mechanically lock in place into a recess 712 formed in the end of the shaft 706. As known in the art, a release mechanism (not shown) may be provided to allow the surgeon to selectively disengage the cutting tip 710 from the shaft 706. Moreover, the surgical bone awl 700 may include a hole-retention sleeve (not shown) which may surround at least part of the shaft 706 and the tip 710 and may be configured to surround the entire shaft 706 and tip 710. The curvature angle β of the curved surgical bone awl 700 may be designed to conform with the curvature angle θ of the pedicle nail 100 (e.g., shown on FIGS. 1A, 1B, and 2). For example, the surgical bone awl 700 may have any suitable curvature angle β.

Figure 8B:
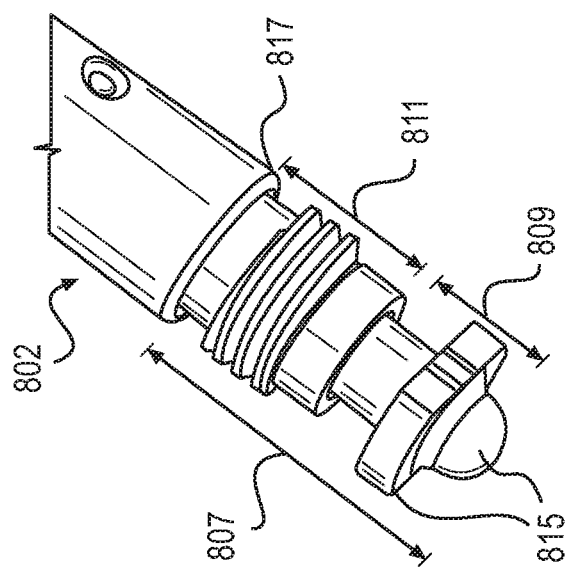
Figure 8A:
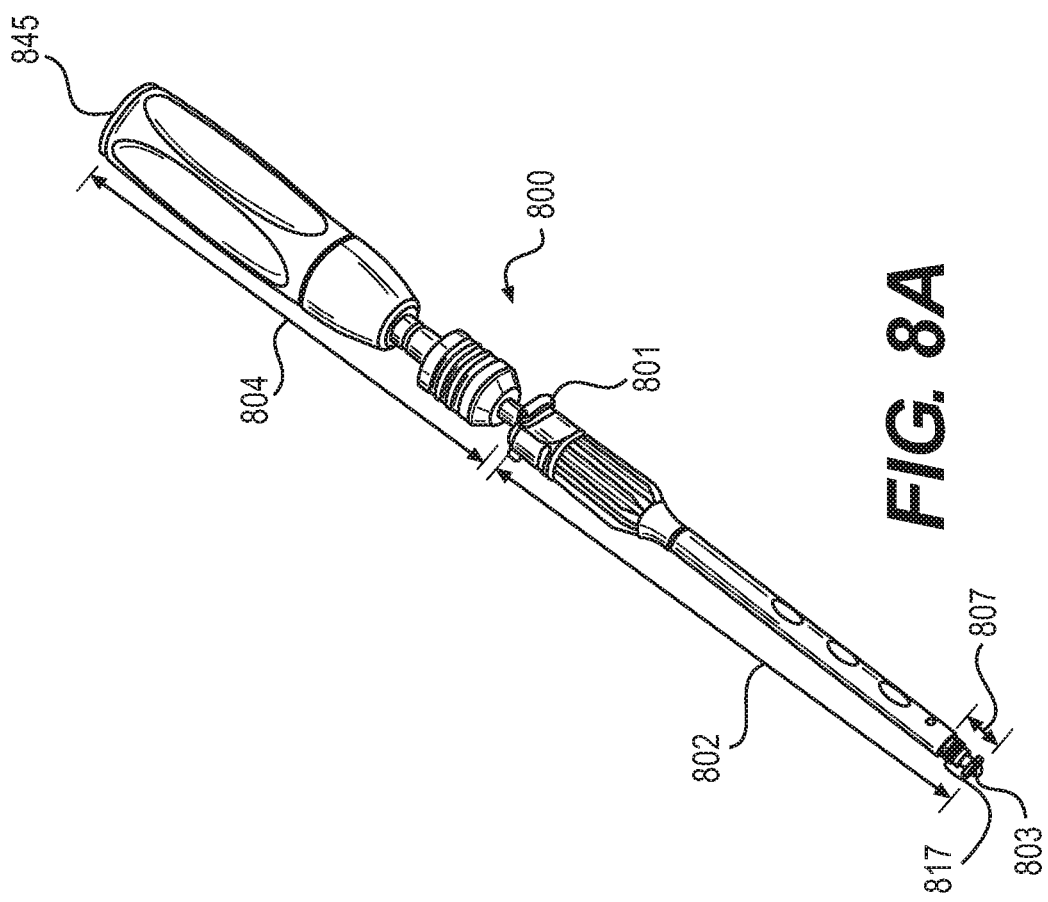

FIGS. 8A, 8B, 8C and 8D illustrate an embodiment of an insertion tool assembly 800 that may be used for insertion of the monoaxial tulip 500. As illustrated, the insertion tool assembly 800 may comprise a proximal end 845 and a distal end 803, wherein the proximal end 845 of the insertion tool assembly 800 may comprise a driver 804. The driver 804 may comprise a proximal end 901 (see FIG. 9A) and a distal end 903 (see FIG. 9A). The distal end 803 of the insertion tool assembly 800 may comprise an insertion tool 802. The insertion tool 802 may comprise a proximal end 801 and a distal end 817, wherein the distal end 903 of the driver 804 may be removably connected to the proximal end 801 of the insertion tool 802. Referring to the exploded view of FIG. 8B, the distal end of the insertion tool 817 may comprise a retractable locking assembly 807. The retractable locking assembly 807 may be a threaded shaft locking assembly for the monoaxial tulip 500. More specifically, the retractable locking assembly 807 may be seated in the insertion tool assembly interface 502 of the monoaxial tulip 500. The retractable shaft locking assembly 807 may include an inner shaft 809 and an outer shaft 811. As depicted in FIG. 8C and the exploded view of FIG. 8D, the retractable shaft locking assembly 807 may be retracted to allow the outer shaft 811 to be threaded into the monoaxial tulip 500.

Figure 9A:
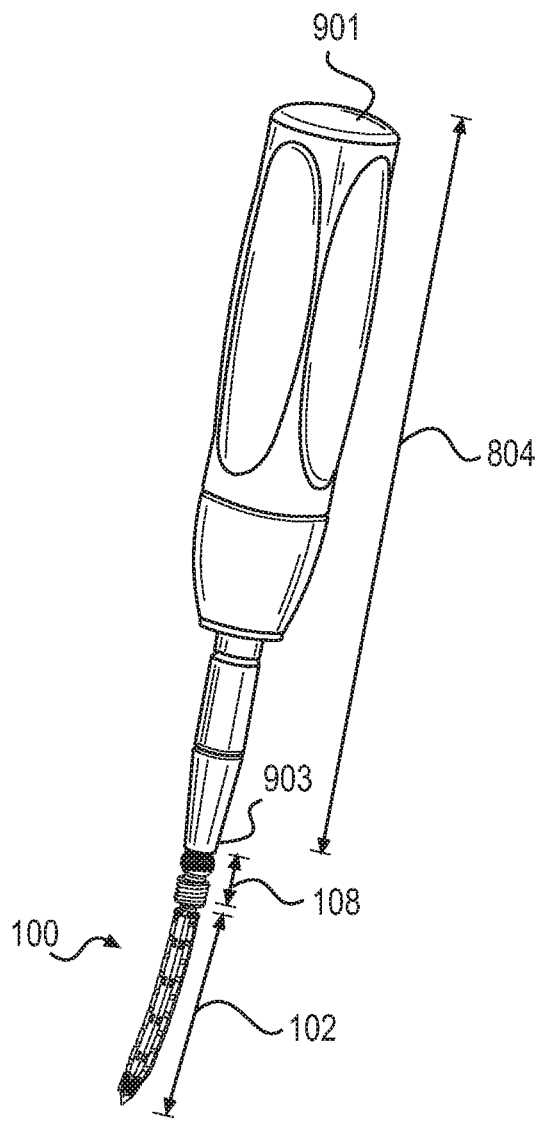
FIGS. 9A and 9B illustrate a driver coupled with a pedicle nail system.
Figure 9B:
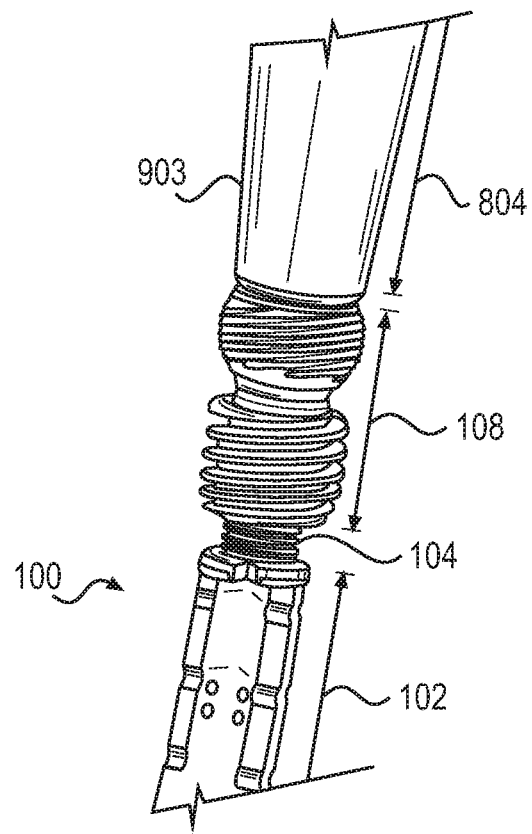

FIGS. 9A and 9B illustrate an embodiment of a driver 804 coupled with a pedicle nail 100. As illustrated, the pedicle nail 100 may comprise a shank 102 and a nail head 108. As depicted, the distal end 903 of the driver 804 may be coupled to the insertion tool assembly interface 306 of the nail head 108. Referring to the exploded view of FIG. 9B, the driver 804 may be directly coupled to the insertion tool assembly interface 306, wherein the interface 306 may be positioned within the proximal end 104 of the nail head 108, wherein the nail head 108 may be threadably connected to the mounting threads 216 positioned at the proximal end 104 of the pedicle nail 100.

FIGS. 10A and 10B illustrate an embodiment of a curved awl 700 creating a pathway for insertion of a pedicle nail 100. As illustrated, the curved awl 700 may create a pathway for insertion of the pedicle nail 100 into a cortical bone 1002, wherein the pathway may be created by maneuvering the cutting tip 704. As known in the art, a release mechanism (not shown) may be provided to allow the surgeon to selectively disengage the cutting tip 710 from the shaft 706. Moreover, the curved awl 700 may include a hole-retention sleeve (not shown) which may surround at least part of the shaft 706 and may be configured to surround the entire shaft 706 and tip 710. The curvature angle β of the curved surgical bone awl 700 may be designed to conform with the curvature angle θ of the pedicle nail.

FIGS. 11A and 11B illustrate an embodiment of a pedicle nail 100, including a driver 804, with a tamping device 1102 driving the pedicle nail 100 into a cortical bone 1002. As depicted, the pedicle nail 100 may comprise a shank 102 with a nail head 108. The driver 804 may be coupled to the nail head 108 at the insertion tool interface 306. As further illustrated in FIG. 11B, the pedicle nail 100 and the driver 804 may be tamped down with a tamping device 1102 up to and until the nail head 108 contacts the cortical bone 1002.

FIGS. 12A and 12B illustrate a polyaxial tulip insertion procedure with an embodiment of the nail head 108 of a pedicle nail 100 being threaded into a cortical bone 1002 with an insertion tool assembly. As illustrated, the nail head 108 may be threaded into the cortical bone 1002. After the nail head 108 has been secured into the cortical bone 1002, a polyaxial tulip 600 may be threadably connected to the tulip threads 109 positioned at the proximal end 302 of the nail head 108.

Figure 13A:
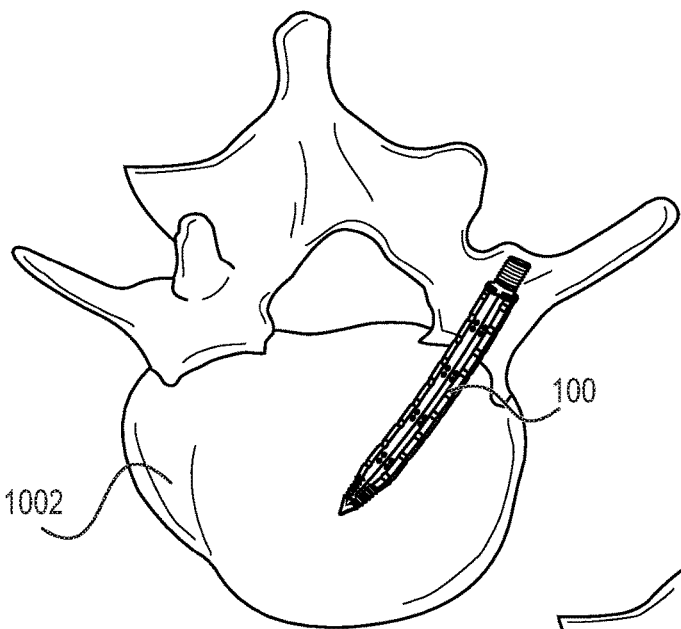
FIGS. 13A, 13B, and 13C illustrate a monoaxial tulip insertion procedure with an embodiment of the nail head of a pedicle nail system being threaded into the cortical bone with an insertion tool assembly.
Figure 13B:
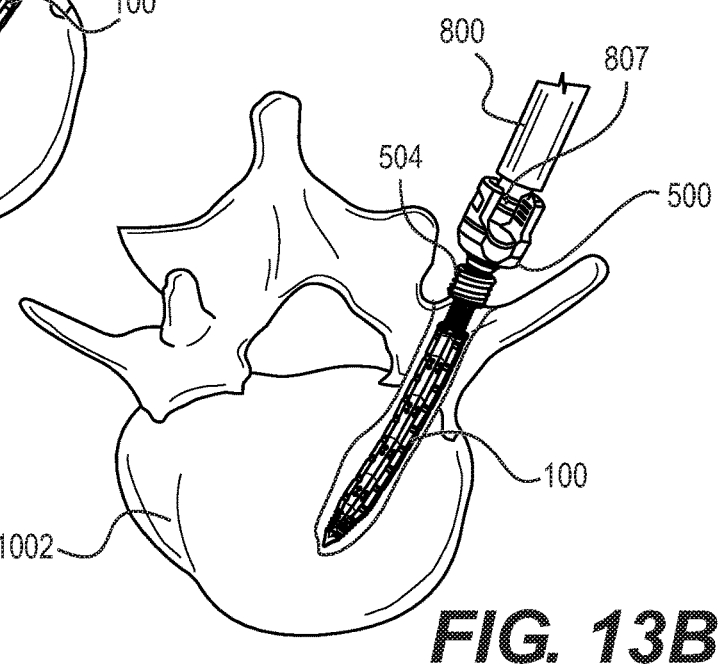
Figure 13C:
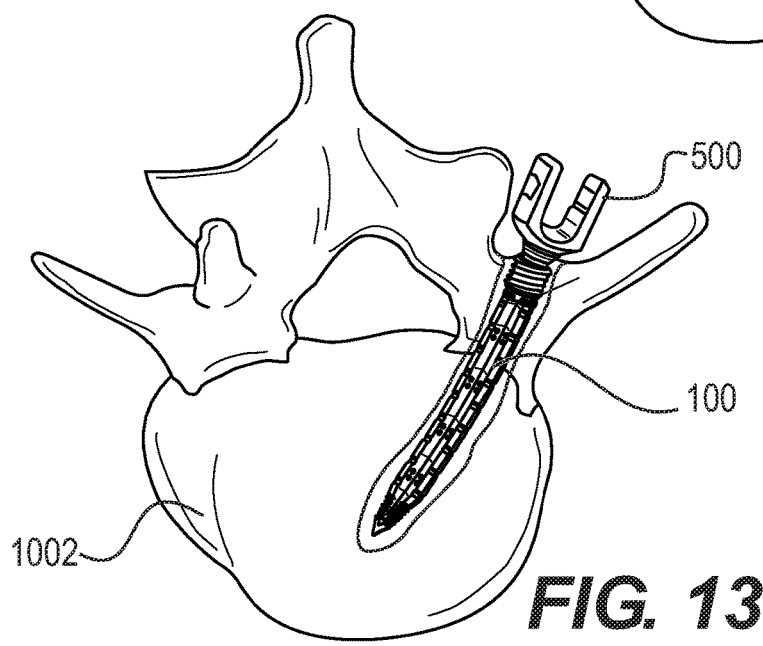

FIGS. 13A, 13B, and 13C illustrate a monoaxial tulip insertion procedure with an embodiment of the pedicle 100. As illustrated on FIG. 13A, the nail head 108 (not shown) may be removed from the pedicle nail 100 after tamping of the pedicle nail 100 into the cortical bone 1002. As illustrated on FIG. 13B, monoaxial tulip 500 may be attached to pedicle nail 100. In the illustrated embodiment, the insertion tool assembly 800 may be used to attach the monoaxial tulip 500 to the pedicle nail 100. By clockwise rotation of the insertion tool assembly 800, the bone threads 504 of the monoaxial tulip 500 may be threadably secured to the cortical bone 1002. After the pedicle nail 100 and monoaxial tulip 500 have been secured in the desired location, the insertion tool assembly 800 may be withdrawn, as shown on FIG. 13C, and the surgical rods (not shown) may then be implanted.

Figure 14A:
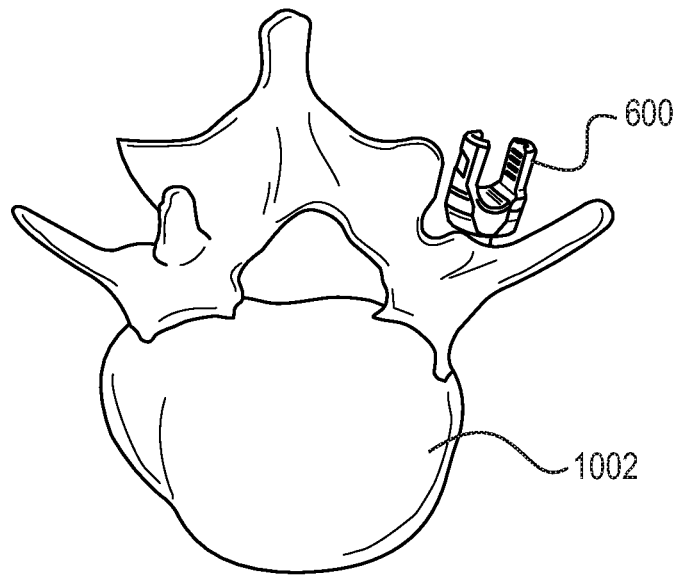
FIGS. 14A and 14B illustrate the final placement of tulips in relation to the cortical bone.
Figure 14B:
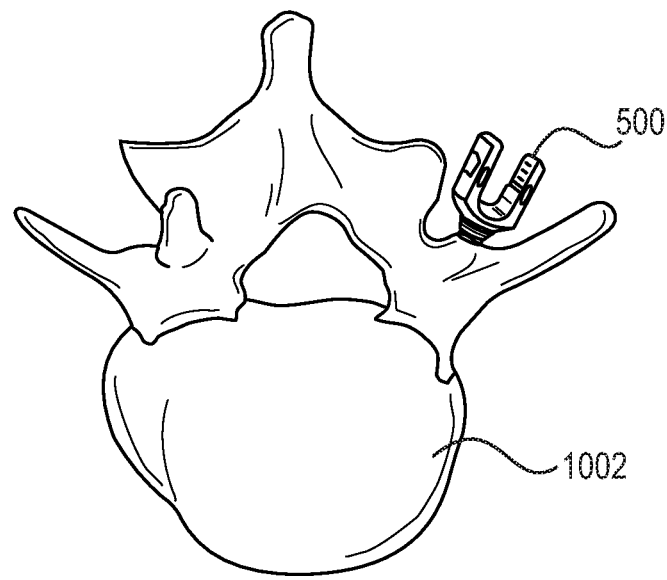

FIGS. 14A and 14B illustrate the final placement of tulips in relation to the cortical bon 1002. As illustrated on FIG. 14A, the polyaxial tulip 600 may be positioned on the cortical bone 1002 with the pedicle nail 100 (not shown) disposed in the cortical bone 1002. As illustrated on FIG. 14B, the monoaxial tulip 600 may be positioned on the cortical bone 1002 with the pedicle nail 100 (not shown) disposed in the cortical bone 1002.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pedicle nail comprising
   a shank comprising a proximal end and a distal bone engagement end, wherein the proximal end has mounting threads; and
   a nail head disposable on the proximal end of the shank and configured to threadably engage with the mounting threads, the nail head having external bone threads configured to engage bone to secure the nail head to the bone,
   wherein a pitch of the bone threads is greater than a pitch of the mounting threads such that the shank is pulled toward the nail head during implantation,
   wherein the shank is a curved shank, having a curvature angle θ,
   wherein the nail head includes tulip threads for engaging with a tulip, and
   wherein the nail head is a separate element from the shank and the tulip.

2. The pedicle nail of claim 1, wherein the shank comprises fenestrated perforations about the longitudinal axis thereof, wherein the number of fenestrated perforations can range from 2 to 100.

3. The pedicle nail of claim 2, wherein the shank comprises at least two protrusions configured along the longitudinal axis thereof, wherein the protrusions form channels along the longitudinal axis, wherein the protrusions have an exposed vertical edge, wherein the vertical edge has at least two notches, wherein the notches are in vertical alignment with one another.

4. The pedicle nail of claim 1, wherein the nail head has a proximal end and a distal end, wherein the distal end of the nail head threadably engages with the proximal end of the shank, and wherein the proximal end of the nail head comprises an insertion tool assembly interface therein.

5. A pedicle nail system comprising:
   a pedicle nail, wherein the pedicle nail comprises a shank and a nail head, wherein the shank comprises a proximal end and a distal bone engagement end, wherein the proximal end comprises shank mounting threads attached thereto, wherein the nail head has nail head mounting threads configured to threadably receive the shank mounting threads, wherein the nail head has external bone threads configured to engage bone and secure the nail head to the bone, wherein a pitch of the bone threads is greater than a pitch of the shank mounting threads such that the shank is pulled toward the nail head during implantation; and
   a tulip, wherein the tulip comprises a proximal end and a distal end,
   wherein the shank is a curved shank, having a curvature angle θ,
   wherein the nail head includes tulip threads for engaging with the tulip, and
   wherein the nail head is a separate element from the shank and the tulip.

6. The pedicle nail system of claim 5, wherein the shank has fenestrated perforations along the longitudinal axis thereof, wherein the number of fenestrated perforations range from 2 to 100, and wherein the shank comprises at least two protrusions configured along the longitudinal axis thereof, wherein the protrusions form channels along the longitudinal axis of the shank.

7. The pedicle nail system of claim 5, wherein a proximal end of the nail head comprises an insertion tool assembly interface therein.

8. The pedicle nail system of claim 7, wherein the tulip is a polyaxial tulip threadably attached to the proximal end of the nail head.

9. A pedicle nail system comprising:
   a pedicle nail, wherein the pedicle nail comprises a shank and a nail head, wherein the shank comprises a proximal end and a distal bone engagement end, wherein the proximal end comprises shank mounting threads attached thereto, wherein the nail head has nail head mounting threads configured to threadably receive the shank mounting threads, wherein the nail head has external bone threads configured to engage bone and secure the nail head to the bone, wherein a pitch of the bone threads is greater than a pitch of the shank mounting threads such that the shank is pulled toward the nail head during implantation; and
   a tulip wherein the tulip comprises a proximal end and a distal end, wherein the distal end of the tulip is configured to be mounted on the pedicle nail; and
   a driver, wherein the driver comprises a proximal end and a distal end; wherein the distal end of the driver is removably connected to the proximal end of the pedicle nail,
   wherein the shank is a curved shank, having a curvature angle θ,
   wherein the nail head includes tulip threads for engaging with the tulip, and
   wherein the nail head is a separate element from the shank and the tulip.

10. The pedicle nail system of claim 9, wherein the shank has fenestrated perforations along the longitudinal axis thereof, wherein the number of fenestrated perforations can range from 2 to 100.

11. The pedicle nail system of claim 9, wherein a proximal end of the tulip comprises an insertion tool assembly interface therein.

12. The pedicle nail system of claim 11, wherein an insertion tool assembly is attachable to the insertion tool assembly interface of the tulip.

* * * * *